United States Patent [19]

Kondo et al.

[11] 4,367,309

[45] Jan. 4, 1983

[54] GLYCOPROTEIN DERIVATIVE COMPOSITIONS, PROCESS FOR PRODUCING THE SAME AND USES THEREOF AS DIAGNOSTIC REAGENTS OR HYDROLYTIC CATALYSTS

[75] Inventors: Shigeharu Kondo, Kyoto; Junichiro Kikutake, Neyagawa; Masakazu Sugiura, Nara; Masaru Yoshida, Kyoto, all of Japan

[73] Assignee: Sanyo Chemical Industries, Ltd., Kyoto, Japan

[21] Appl. No.: 8,107

[22] Filed: Jan. 31, 1979

[30] Foreign Application Priority Data

Feb. 24, 1978 [JP] Japan .................................. 53-21225

[51] Int. Cl.$^3$ .............................................. C08L 89/00
[52] U.S. Cl. .............................. 525/54.1; 260/112 R; 424/85; 435/176; 435/178; 435/179; 435/181; 435/188
[58] Field of Search .......................... 260/112 R, 6, 8; 435/188, 176, 179, 178, 181; 424/85; 525/54.1

[56] References Cited

U.S. PATENT DOCUMENTS

| | | | |
|---|---|---|---|
| 3,519,538 | 7/1970 | Messing | 195/63 |
| 3,846,306 | 11/1974 | Barker et al. | 260/6 |
| 3,970,521 | 7/1976 | Zaborsky | 195/63 |
| 4,169,014 | 9/1979 | Goldberg | 435/182 |
| 4,217,338 | 8/1980 | Quash | 424/1 |

FOREIGN PATENT DOCUMENTS

| | | |
|---|---|---|
| 2534412 | 2/1976 | Fed. Rep. of Germany . |
| 2651680 | 5/1977 | Fed. Rep. of Germany . |
| 2132080 | 11/1972 | France . |
| 2322155 | 3/1977 | France . |

*Primary Examiner*—Allan Lieberman
*Assistant Examiner*—Pat Short
*Attorney, Agent, or Firm*—Oblon, Fisher, Spivak, McClelland & Maier

[57] ABSTRACT

Highly stable glycoprotein derivative compositions showing little tendency to decrease in physiological activity thereof are produced by reacting an aldehyde-group-containing glycoprotein (A) with an SH- or OH-containing material (B), and if necessary further reacting the resulting product with an SH- or OH-containing material of the same or another kind. They are used as diagnostic reagents or hydrolytic catalysts.

27 Claims, No Drawings

GLYCOPROTEIN DERIVATIVE COMPOSITIONS, PROCESS FOR PRODUCING THE SAME AND USES THEREOF AS DIAGNOSTIC REAGENTS OR HYDROLYTIC CATALYSTS

BACKGROUND OF THE INVENTION

1. Field of the Invention

This invention relates to a process for producing glycoprotein derivative compositions, the products and uses thereof. More particularly, it relates to a process for producing glycoprotein compositions suitable for use as insolubilized glycoproteins or for labelling purposes, products and uses thereof.

2. Description of the Prior Art

Recently, physiologically active glycoproteins rendered water-insoluble have widely been used in synthesis, decomposition, separation, purification or analysis of a variety of substances, or in labelling certain substances for analysis purposes. The so-far known methods of insolubilizing glycoproteins through convalent bonds or of labelling other substances with glycoproteins make use of a functional group or functional groups (such as α- or ε-amino, α-, β- or γ-carboxyl, sulfhydryl, hydroxyl, imidazolyl or phenyl) being present in the protein portion of a glycoprotein molecule.

These methods of binding glycoproteins to other substances, however, have their drawbacks such that in some cases effective binding cannot be achieved because of an insufficient or too small amount of available functional groups such as mentioned above; and that those functional groups, which in many cases play important roles in manifestation of their physiological activities, lose such activities entirely or considerably as a result of their being bound.

Lately a process has been developed for producing glycoprotein derivatives by oxidizing a carbohydrate portion of the glycoprotein to a carbonyl group and reacting the resultant carbonyl group with an amino group of an amino-containing material. The stability of the derivatives produced by this process cannot be satisfied as yet.

SUMMARY OF THE INVENTION

Under these circumstances, the inventors have made extensive research works to eliminate those drawbacks in the prior arts and finally accomplished the present invention.

Accordingly, it is an object of this invention to provide highly stable glycoprotein derivative compositions (or conjugates), process for producing the same and uses thereof as diagnostic reagents or hydrolytic catalysts.

Another object of the invention is to provide glycoprotein derivative compositions (or conjugates) showing smaller loss in physiological activity originating from the starting glycoprotein, namely, having activity substantially equivalent to the glycoprotein as compared with conventional glycoprotein derivatives.

Briefly these and further objects of the invention as hereinafter will become more readily apparent have been attained broadly by providing process for producing a glycoprotein derivative composition reacting an aldehyde group-containing glycoprotein (A) with at least one SH or OH group containing material (B).

DETAILED DESCRIPTION OF THE PREFERRED EMBODIMENTS (A) Aldehye group-containing glycoproteins The term "glycoprotein" used herein means a conjugated protein which contains in its molecule a carbohydrate (or a derivative thereof). The content of the carbohydrate portion in the glycoprotein is not specifically limited, but preferably it is 1 to 70% by weight, more preferably 5 to 50% by weight. The carbohydrate portion is not particularly critical; and suitable ones include, for example, hexosamines (such as glucosamine, galactosamine), hexoses (such as mannose, galactose), hexuronic acids (such as glucuronic acid, galacturonic acid), and the like. The glycoprotein is not particularly critical. Suitable examples of the glycoproteins are ovalbumin (or egg albumin); antibodies such as γ-globulin; enzymes (glycoenzymes) such as β-galactosidase, α-amylase, glucoamylase, glucose oxidase, peroxidase, invertase and so on. Among the glycoproteins, enzymes and antibodies are most useful.

In reacting with at least one SH or OH group-containing material to form glycoprotein derivatives according to this invention, it is essential for the glycoprotein to contain at least one aldehyde group in its carbohydrate portion. The aldehyde group can be formed by oxidizing carbohydrate portion with an oxidizing agent or may be the one originally existing in the molecule. The glycoproteins having a ketone (or carbonyl) group in the carbohydrate portion thereof may also be used.

As is well known, oxidation of the carbohydrate portion or moiety of glycoproteins leads to formation of aldehyde groups and a variety of oxidizing agents can be used for said oxidation. Examples of the oxidizing agents are metal salts, such as lead tetraacetate, manganic acetate, cobalt acetate, thallic acetate, and ceric sulfate; and oxygen acids and salts thereof, such as periodic acid, paraperiodic acid, sodium metaperiodate and potassium metaperiodate. Among these, oxygen acids and salts thereof are preferred in view of the fact that peroxidation hardly takes place and secondary or side reactions are infrequent when such are used.

Oxidation of the glycoproteins with these oxidizing agents can be carried out by known method. In the oxidation, the glycoprotein is used generally in the form of an aqueous solution, the concentration being generally 0.1 to 100 mg/ml, preferably 1 to 50 mg/ml. When an oxygen acid or a salt thereof is used as the oxidizing agent, it is used generally in the form of an aqueous solution, and the concentration is generally 0.001 to 10 M and preferably 0.01 to 0.1 M. The amoun of the oxygen acid or salt thereof depends on the kind of the glycoprotein, but generally it is used in excess, for example, twice to ten times as much as the amount of the carbohydrate portion contained in the glycoprotein. The optimal amount, however, can be determined by experiments.

In the process for oxidizing glycoproteins with oxygen acids or salts thereof, the pH value of the reaction solution is generally 3 to 10, preferably 4 to 8. The reaction temperature is generally 0° to 50° C., preferably 5° to 20° C. The reaction period is generally 5 minutes to 24 hours, preferably 15 minutes to 3 hours.

When a sufficient quantity of aldehyde groups has been formed for reaction with an SH- or OH-containing material in the next step, it is preferable to add a polyhydric alcohol, such as ethylene glycol or glycerol, so as to terminate the reaction and thereafter to remove contaminant low-molecular-weight substances by dialysis or any other appropriate method so as to leave the oxidized glycoprotein only. For the purpose of removing the low-molecular-weight contaminants by dialysis, buffer solutions at a concentration of 0.01 M and with a pH of 4 to 9, for example, are usable.

In cases where blocking of the amino group of the glycoprotein is not a hindrance to the contmplated use of the derivative, it is preferred to block the amino group of the glycoprotein prior to oxidation thereof so that the yield of the contempiated derivative can be improved. As an example of the amino blocking method may be mentioned the method described in Biochemical Journal 39, 507–515 (1945).

During the oxidation of the glycoprotein with an oxygen acid or a salt thereof, light is preferably excluded to prevent over oxidation of the glycoprotein.

(B) SH- or OH-containing materials

No particular limitation is imposed on the kind of the SH- or OH-containing material, so long as it contains at least one free SH or OH group. The SH- or OH-containing material may be either water-soluble or water-insoluble.

(1) Examples of suitable water-soluble SH- or OH-containing materials are water-soluble thioalcohols (such as ethyl mercaptan); water-soluble alcohols (such as ethanol) and SH- or OH-containing peptides including oligopeptides, and proteins (polypeptides) such as enzymes (such as lipase, papain, trypsin), antibodies [such as anti insulin, anti AFP (anti α-fetoprotein)] and the like. Antibodies are especially useful.

Other examples of suitable water-soluble SH- or OH-containing materials are those products that have obtained by intorducing at least one SH or OH group into water-soluble materials by various chemical methods (for example by using sulfhydrylating agents as hereinafter described or hydroxylating agents). The water-soluble materials, into which an SH or OH group be introduced, is not particularly critical. Such materials are, for example, peptides including oligopeptides and proteins such as enzymes and antibodies (said peptides may either have or have not an SH or OH group); and water-soluble polymers such as polyvinyl alcohol, hydroxyethyl (meth)acrylate polymers and polyoxyalkylene ethers having oxyethylene contents of not less than 50%. The peptides include the above-mentioned SH- or OH-containing peptides, and other peptides. Especially useful are antibodies.

(2) As examples of the water-insoluble SH- or OH-containing materials, there may be mentioned natural and synthetic polymers having SH or OH groups. Such natural polymers include, for example, cellulose and starch. Examples of such synthetic polymers include polyurethanes having terminal SH or OH groups [reaction products of polyisocyanates (such as tolylene diisocyanate) with excess of active hydrogen atmos-containing material having at least one SH or OH group (such as polypropylene glycol)], copolymers of SH- or OH-containing vinyl monomers [such as hydroxyalkyl (meth)acrylates, $CH_2=CH-CONHCH(COOH)CH_2SH$, and the like], and polythiols [such as mercapto-derivatives of vinyl polymers (such as polyacrylamide), for example, "Enzacryl Polythiol" available from Koch-Lite Laboratories Ltd., Great Britain].

Other examples of suitable water-insoluble SH- or OH-containing materials include those products obtained by introducing at least one SH or OH group into water-insoluble materials by various chemical methods (for example by use of a sulfhydrylating or hydroxylating agent).

The water insoluble materials into which an SH or OH group is to be introduced are not particularly restricted, but especially useful are solid materials. Suitable ones include, for example, glasses, silica, metals (such as iron, cobalt, nickel, aluminum, magnesuim, copper, zinc, silver, gold), metal oxides (such as ferric oxide, triiron tetroxide aluminum oxide, zinc oxide), and polymers such as olefin polymers (such as polyethylene, polypropylene), styrene polymers, acrylic polymers, polyurethanes, polyamides, polyimides, polyamino acids, polysaccharides and derivative thereof, (such as cellulose and derivatives thereof, agarose and derivatives thereof). Preferably these water-insoluble materials are porous so that a relatively large amount of the glycoprotein can be bound to each unit weight of the water-insoluble materials.

Even in the case of a material having an SH or OH group by nature but in a small proportion, it is preferable to introduce into it an SH or OH group by various chemical methods before use, that is prior to reaction with the glycoprotein.

Various methods can be employed for introducing an SH or OH group into various materials (water-soluble or water-insoluble materials). Introduction of an SH or OH group can be carried out by using a sulfhydrylating or hydroxylating agent, namely a compound having an SH or OH group [or a precursor thereof (such as acylated SH or OH group)] and a functional group reactive with said material. Examples of such functional groups include carboxyl group, carboxylic acid anhydride group, amino group (primary- and secondary-), epoxy group, hydroxyl group, mercapto group, alkoxysilyl groups (such as methoxy- or ethoxy-substituted silyl groups), halosilyl groups (such as chloro-substituted silyl groups) and the like. Preferred example of such methods are (1) the methods described in Archives of Biochemistry and Biophysics 96,605–612 (1962) using such sulfhydrylating or hydroxylating agent as an S-acylmercapto-containing acid anhydride (e.g. S-acetylmercaptosuccinic anhydride) or an O-acylhydroxyl-containing acid anhydride (e.g. O-acetylhydroxysuccinic anhydride) and (2) the methods described in Science 166, 615–617 (1969) so modified as to use, in place of γ-aminopropyltriethoxysilane, a sulfhydrylating or hydroxylating agent including an SH- or OH-containing silane coupling agent [for example mercaptoalkyltrialkoxysilanes (such as γ-mercaptopropyltrimethoxysilane), hydroxyalkyltrialkoxysilanes (such as γ-hydroxypropyltrimethoxysilane) and the like]. The method (1) above is especially suited for the introduction of an SH or OH group into water-soluble proteins and so on, while the method (2) is suitable for introducing an SH or OH group into water-insoluble materials, especially inorganic materials.

In method (1), an S-acylmercaptosuccinic anydride (preferably S-acetylmercaptosuccinic anhydride) or an O-acylhydroxysuccinic anhydride (preferably O-acetylhydroxysuccinic anhydride) is used in an amount of usually 10 to 300 parts by weight, preferably 100 to 200 parts by weight, per 100 parts by weight of a material into which an SH or OH group is to be introduced. The reaction is carried out preferably in a 0.1 M phosphate buffer solution. The pH of the reaction solution is generally 5 to 8, preferably 6 to 7. The reaction temperature is, for example, 0° to 50° C., preferably 10° to 20° C. The reaction period is generally 10 minutes to 2 hours, preferably 20 minutes to an hour. After the reaction, low molecular weight substances may be removed by subjecting the reaction product to gel filtration through a Sephadex G-25 column, for instance. Then deacetylation can be effected, for example, by adding about 0.1 part by volume (per part by volume of the purified reaction product) of an aqueous hydroxylamine solution having a concentration of usually 0.01 to 2 M, preferably 0.1 to 1 M (or mol/l). In carrying out the deacetylation, pH of the reaction solution is generally 5 to 9, preferably 6 to 8. The reaction temperature is, for example, 0° to 40° C., preferably 20° to 40° C. The reaction period is usually 5 minutes to 2 hours, preferably 10 to 30 minutes. Again, the reaction mixture is subjected to gel filtration by passing through the same Sephadex G-25 column, for instance, for the purpose of purifying the resulting SH- or OH-containing material.

In method (2), the SH- or OH-containing silane coupling agent is used in an amount of generally 0.1 to 100 parts by weight, preferably 1 to 50 parts by weight, per 100 parts by weight of the material into which an SH or OH group is to be introduced. For example, to the material into which an SH or OH group is to be introduced is added a 0.1 to 10% (V/V) solution of SH or OH-containing silane coupling agent (such as γ-mercaptopropyltrimethoxysilane or γ-hydroxypropyltrimethoxysilane) in acetone. The mixture is allowed to stand at room temperature for 10 minutes to 10 hours, then the supernatant liquid is removed, and the residue is washed thoroughly with acetone, dried and stored.

In addition to the above two methods, the following methods can also provide SH- or OH-containing materials: (3) the method comprising reacting an amino-containing material with a thioglycolide or an N-acyl-homocysteine thiolactone, preferably N-acetyl-homocysteine thiolactone; (4) the method comprising reacting a CNBr-activated agarose with a compound of the general formula $NH_2-R-SH$ (R being an alkylene); (5) the method comprising adding an alkylene oxide or ethylene chlorohydrin or the like to an active-hydrogen-containing polymer such as a polyamide, a polymide or cellulose; and (6) the method comprising hydrolyzing a copolymer derived from a monomer capable of producing an OH group on hydrolysis, such as acetate.

In view of the greater reactivity and of the higher stability of the derivatives, SH-containing materials are preferred to OH-containing materials.

(C) Production of glycoprotein derivative compositions

The production of the glycoprotein derivative compositions according to this invention is carried out by reacting an aldehyde group-containing glycoprotein (A) with an SH- or OH-containing material (B), and if necessary further reacting the resulting product with said material (B) or another SH- or OH-containing material. Thus, more detailedly, the production is realized by the one-step method comprising reacting glycoprotein (A) with material (B); or by the two-step method comprising first reacting glycoprotein (A) with an SH- or OH-containing material ($B_1$) and then reacting the resulting product with material ($B_1$) or another SH- or OH-containing material ($B_2$). In the latter method, there may be used, for example, a water-insoluble SH- or OH-containing material as material ($B_1$) and a water-soluble SH- or OH-containing material as material ($B_2$).

The above reactions proceed in accordance with the following reaction equations, giving products mainly consisting of glycoprotein derivatives having a hemithioacetal- or hemiacetal-linkage (Derivatives I) or/and glycoprotein derivatives having a thioacetal or acetal bond (Derivatives II):

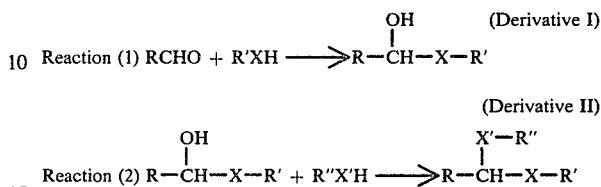

wherein, in the formulas, R is glycoprotein residue, X and X' are each independently O or S, and R' and R'' are each independently residue of an SH- or OH-containing material. Derivatives I produced by reaction (1) can, if desired, be converted into derivatives II by reacting derivatives I further with material (B) or another SH- or OH-containing material.

In binding an aldehyde group-containing glycoprotein with an SH- or OH-containing material according to the invention, the weight ratio between the aldehyde group-containing glycoprotein and the SH- or OH-containing material is not specifically limited, but can be varied in a wide range, and is generally from 1000:1 to 1:1000, preferably from 100:1 to 1:100, more preferably from 10:1 to 1:10.

The aldehyde group-containing glycoprotein and the SH or OH group-containing material are reacted under conditions suited for the formation of hemithioacetal-or hemiacetal-linkages and/or thioacetal-or acetal-linkages.

In cases where a water-soluble SH- or OH-containing material is reacted with an aldehyde group-containing glycoprotein, the SH- or OH-containing material is generally subjected to the reaction in the state of an aqueous solution, wherein the concentration of the aqueous solution of said SH- or OH-containing material is generally 0.001 to 50% (W/W), preferably 0.01 to 10% (W/W). The concentration of the aqueous solution of the aldehyde group-containing glycoprotein is generally 0.001 to 50% (W/W), preferably 0.01 to 10% (W/W). The pH of the reaction system is generally 3 to 10, preferably 4 to 8, more preferably 4.5 to 5.4. The reaction temperature is generally 0° to 50° C., preferably 10° to 20° C. The reaction period is generally 10 minutes to 24 hours, preferably 30 minutes to 3 hours.

In cases where a water-insoluble SH- or OH-containing material is reacted with an aldehyde group-containing glycoprotein, generally 1,000 to 10,000 parts by weight of an aqueous solution of the aldehyde group-containing glycoprotein having a concentration generally of 0.01 to 50% (W/W), preferably of 0.1 to 10% (W/W), is used per 100 parts by weight of the water-insoluble SH- or OH-containing material. The SH- or OH-containing material can be added in the form of a solid (powder or granules) or as an aqueous dispersion. The pH of the reaction mixture is generally 3 to 10, preferably 4 to 8. The reaction temperature is generally 0° to 50° C., preferably 10° to 20° C. The reaction period is generally 10 minutes to 24 hours.

The above procedures give derivatives I or II; and in cases where the products are derivatives I, these can be converted into derivatives II by further reacting derivatives I with an SH- or OH-containing material, as occasion arises. Thus, in this case, generally 10 to 10,000 parts by weight of an aqueous solution of an SH- or OH-containing material having a concentration generally of 0.01 to 10% (W/W) is added to the above-mentioned reaction mixture. The SH- or OH-containing material to be used here may be the same as or different from the one used for the production of derivative I. However, water-soluble, and especially low-molecular-weight materials such as ethyl mercaptan, ethyl alcohol, dithioethylene glycol and ethylene glycol are preferred. The pH of the reaction mixture is generally 3 to 10, preferably 4 to 8. The reaction temperature is generally 0° to 50° C., preferably 10° to 20° C. The reaction period is generally 10 minutes to 24 hours, preferably 30 minutes to 5 hours.

In cases where the resulting derivatives are water-soluble, the reaction product can be subjected to gel filtration by passing it through a Sephadex G-100 column, for example, to remove the unreacted SH- or OH-containing material and aldehyde group-containing glycoprotein.

On the other hand, when the resulting derivatives are water-insoluble, the reaction product can be purified, for example, by washing thoroughly with an aqueous 1 M sodium chloride solution followed by washing with a 0.01 M phosphate-buffered physiological saline solution (pH 7.3).

When water-insoluble material is used as at least a part of the SH- or OH-containing material, the resulting derivative (conjugate) maintains the shape and form and consistency of the original SH- or OH-containing material, and therefore it occurs generally as a solid having the appearance of powder, granules, rods, film and so on. When all of the original SH- or OH-containing material is water-soluble, the resulting derivative takes the form of an aqueous solution, and can be used in that state.

(D) Utility of the glycoprotein compositions

The glycoprotein derivatives produced according to the invention can be used for various purposes as substitutes for the conventional glycoproteins and derivatives thereof. They have the following advantages over the conventional glycoproteins and derivatives thereof: (1) The glycoprotein derivatives produced by the process of the present invention have higher thermal stability than the starting glycoproteins, making it possible to use them at higher temperatures than ever; (2) The water-insoluble glycoprotein derivatives produced according to the invention, when packed in columns, for example, can be used repeatedly and available in continuous processes, so that the reaction efficiency and economical efficiency can be improved as compared with the cases where the glycoproteins are used per se; (3) The derivative of this invention show smaller loss in physiological activity originating from the starting glycoprotein, namely, have activity substantially equivalent to the glycoprotein as compared with conventional glycoprotein derivatives; (4) The glycoprotein derivatives of the invention are more stable and can be stored for a longer period of time than the conventional glycoprotein derivatives; they can be stored without change in quality for more than one year in a 0.01-M phosphate buffered physiological saline (pH 7.3) at 4° C. These advantages are more markedly observable in derivatives II.

The glycoprotein derivative compositions produced by the invention can be used as a very convenient form as diagnostic reagents, as catalysts for hydrolysis reactions, and for other purposes.

Diagnostic reagents, to which the glycoprotein derivatives produced by the process of the invention can be applied, include, for example, diagnostic reagents for clinical chemistry, immunohematological diagnostic reagents and immunohistological diagnostic reagent. The use as diagnostic reagents for clinical chemistry includes determination of concentrations of chemical components in body fluids, such as glucose, cholesterol and uric acid. The determination of these body fluid components with the glycoprotein derivative compositions can be carried out by any of the conventional methods, for example, those described in Rinsho Byori (The Japanese Journal of Chemical Pathology), Supplement to vol. 25, page 137 (1977), Analytical Biochemistry 52, 402–414 (1973), and Rinsho Byori, Suplement to vol. 24, page 201 (1976). The use as immunohematological diagnostic reagents includes the use as enzyme conjugated antigens or antibodies, such as peroxidase conjugated human chorionic gonadotropin, peroxidase conjugated IgG, and glycoamylase conjugated insulin, and as hapten conjugated proteins such as penicillenic acid conjugated gelatin.

The method for carrying out immunohematological diagnosis using the glycoprotein derivative composition as enzyme conjugated antigen or enzyme conjugated antibody may be any of the conventional methods, for example, those described in FEBS letters 15, 232–236 (1971), Journal of Biochemistry 73, 1319–1321 (1973) and Igaku no Ayumi (Advances in Medicine) 91, 207–208 (1974). The method for preparing anti-hapten antibodies for use in immunohematological diagnosis by using the glycoprotein derivative as hapten conjugated protein may be any of the known methods, for instance, those described in Journal of Experimental Medicine 112, 1227–1247 (1960). The use as immunohistological diagnostic reagents includes the use in the form of enzyme conjugated antibody such as peroxidase conjugated immunoglobulins. The method of carrying out immunohistological diagnosis using the glycoprotein derivative in the form of an enzyme conjugated antibody may be any of the usual methods, for example, those described in Protein, Nucleic Acid and Enzyme 20, 1007–1013 (1975).

The use of the glycoprotein derivative composition obtained by the process of the invention as hydrolytic catalyst includes the use as hydrolytic catalyst for carbohydrates, such as starch, sucrose and lactose. The glycoprotein derivative composition can be used as carbohydrate hydrolysis catalyst according to any of the conventional methods, for example, those described in Biotecnology and Bioengineering 11, 349–362 (1969), Hakko Kyokai-Shi 28, 391–397 (1970), Biotechnology and Bioengineering 15, 951–962 (1973), ibid. 14, 637–645 (1972), Agricultural Biological Chemistry (Tokyo) 30, 807 ff. (1976), Journal of Fermentation Technology 51, 789–794 (1973) and Biotechnology and Bioengineering 16, 295–313 (1974).

Other uses for the glycoprotein derivative compositions producible by the process of the invention include the following: (1) Uses in analysis, e.g. determination of glucose level, choleserol level, uric acid level and the like in fermentation or in drainage, simple rapid quantitative analysis for $H_2O_2$ in solutions (cf. Analytical Biochemistry 14, 160 ff. (1966); (2) Uses in syntheses, e.g. formation of carbon-halogen bonds; (3) Uses in removal of certain substances, e.g. removal of oxygen from solutions; (4) Uses in separation and purification, e.g. in affinity chromatography using insolubilized glycoproteins (e.g. insolubilized enzymes or antibodies) as adsorbents (cf. Biochemical Journal 117, 257–261 (1970), for instance); (5) Uses in oxidation, e.g. oxidation of glucose, oxidation of phenols, aminophenols, diamines or amino acids in the presence of hydrogen peroxide.

Having generally described the invention, a more complete understanding can be obtained by reference to certain specific examples, which are included for purposes of illustration only and are not intended to be limiting unless otherwise specified.

REFERENCE EXAMPLE 1

Oxidation of peroxidase with periodic acid

Peroxidase [100 mg, RZ(Reinheitszahl)=0.8, product of Toyobo Co., Ltd.] was dissolved in 20 ml of 0.01 M phosphate buffer (pH 6.0). To the solution was added 10 ml of 0.06 M periodic acid. While sheltering the reaction vessel from light, the contents were stirred gently at room temperature for 2 hours. Then, 5 ml of 0.8 M glycerol solution was added and gentle stirring was continued for additional 30 minutes, while keeping the reaction vessel in the dark. Finally, the reaction mixture was dialyzed against 0.01 M phosphate buffer (pH 6.0) at 4° C. over 12 hours. The percentage of decomposition of periodic acid due to the oxidation reaction was determined by the method described in Analytical Chemistry 26, 1092–1093 (1954) comprising measuring the change in abosorbance at 224 nm, and found to be about 70%. The resultant, aldehyde group-containing peroxidase solution was stored at 4° C.

REFERENCE EXAMPLE 2

Oxidation of glucose oxidase with periodic acid

Glucose oxidase (100 mg, product of Toyobo Co., Ltd.) was dissolved in 20 ml of 0.01 M phosphate buffer (pH 6.0), then 2 ml of 1% (V/V) 2,4-dinitrofluorobenzene solution in ethanol was added, and the mixture was stirred gently at room temperature for an hour. Then, 5 ml of periodic acid solution (0.06 M) was added, and gentle stirring was continued for further 2 hours with the reaction vessel being sheltered from light. Thereafter, 5 ml of 0.8 M glycerol solution was added, and the resulting mixture was stirred for 30 minutes while maintaining the reaction vessel in the dark. Finally dialysis was made against 0.01 M phosphate buffer (pH 6.0) at 4° C. over 12 hours. The percentage of decomposition of periodic acid due to the oxidation reaction was about 87%. The aldehyde group-containing glucose oxidase solution thus obtained was stored at 4° C.

REFERENCE EXAMPLE 3

Introduction of SH group into insulin

Ten milligrams (about 240 units) of bovine insulin (Wako Pure Chemical Industries, Ltd.) was dissolved in 5 ml of 0.01 M phosphate buffer (pH 6.2). With stirring by means of a magnetic stirrer, about 2 mg of S-acetylmercaptosuccinic anhydride was added. The pH of the reaction mixture was kept at 6.2 to 6.3 by adding 0.05 N NaOH. (With the progress of mercaptosuccinylation of insulin, the pH value became smaller.) After about 40 minutes of reaction at room temperature, the pH drop apparently stopped, whereby termination of the reaction was confirmed. The reaction mixture was then passed through a Sephadex G-25 column (1.5×40 cm) equilibrated with 0.01 M phosphate buffer (pH 6.0) containing 0.1 M NaCl, to separate insulin fractions from other low-molecular-weight compounds. The fractions showing an absorption at 280 nm were combined (about 8 ml), 0.8 ml of 0.5 M hydroxylamine solution (pH 7.3) was added thereto, and the mixture was allowed to stand at 30° C. for 20 minutes. The resulting mixture was again passed through the same Sephadex column as above, to separate the resulting SH-containing (or sulfhydrylated) insulin from other low-molecular-weight compounds. There was obtained about 5 ml of an SH-containing insulin solution. The SH group determination carried out according to the method described in Archieves of Biochemistry and Biophysics 119, 41–49 (1967) revealed that the SH group had been introduced in the proportion of 1.0 to 1.2 molecules per insulin molecule.

REFERENCE EXAMPLE 4

Introduction of SH group into porous glass

To 1 g of porous glass CPK-550 (Corning Glass Works) was added 5 ml of a 2% (V/V) solution of γ-mercaptopropyltrimethoxysilane (Shin-Etsu Chemical Co., Ltd.) in acetone. The mixture was kept at room temperature under a reduced pressure (50 to 100 mmHg) for 5 minutes, so that air in the pores in said porous glass could be removed, and then the reaction was allowed to proceed with gentle stirring at room temperature for 2 hours. The supernatant acetone solution was removed, and the glass was washed thoroughly with acetone, dried, and stored. The quantity of the SH group that had been introduced was determined by the method described in Archives of Biochemistry and Biophysics 82, 70–77 (1959), and it was revealed that about 300 μM of SH group had been introduced per gram of the porous glass.

EXAMPLE 1

Reaction of aldehyde group-containing peroxidase and SH-containing insulin

Half a milliliter (0.5 ml) of the peroxidase solution prepared in Reference Example 1 and 5 ml of the SH-containing (sulfhydrylated) insulin obtained in Reference Example 3 were mixed, and the mixture was allowed to stand at 30° C. for 30 minutes. Thereafter the pH was adjusted to 7.0 with 1 N NaOH, and in order to stabilize the enzyme activity, 0.1 ml of 5% bovine serum albumin and 10 μl of 1 M $MgCl_2$ were added. The resultant mixture was passed through a Sepharose 6B column (1.5×50 cm) equilibrated with 0.01 M phosphate buffer (pH 7.0) containing 0.1 M NaCl, 1 mM $MGCl_2$ and 0.1% bovine serum albumin, to give about 20 ml in total of peroxidase-conjugated insulin fractions. The peroxidase-conjugated insulin solution thus obtained was stored at 4° C.

EXAMPLE 2

Reaction of aldehyde group-containing glucose oxidase and SH-containing porous glass Two grams of the SH-containing porous glass prepared in Reference Example 4 was thrown into the aldehyde group-containing glucose oxidase solution (50 ml) prepared in Reference Example 2 by oxidation of glucose oxidase and containing about 100 mg of the aldehyde group-containing glucose oxidase. The mixture was maintained under a reduced pressure (50 to 100 mmHg) for 5 minutes so as to remove the air in the porous glass. Then the reaction was allowed to proceed at room temperature with gentle stirring for an hour. Thereafter 10 ml of aqueous 0.5% (V/V) ethyl mercaptan solution was added, and stirring was continued at temperature for additional 2 hours. After the reaction, the supernatant was removed, and the glass was washed thoroughly with 1 M aqueous solution of sodium chloride until the washings showed no enzyme activity any more. Finally the glass was washed with 0.01 M phosphate-buffered physiological saline (pH 7.3), immersed in the same saline and stored at 4° C. The amount* of the glucose oxidase bound to the porous glass was 41 mg/g of porous glass.

*Method of calculating the amount of bound glucose oxidase: The absorbance at 280 nm of the oxidized glucose oxidase solution was measured before and after the reaction, and the ratio of binding of the oxidized glucose oxidase to the porous glass was calculated. The amount of bound glucose oxidase was calculated from said ratio of binding, the amount of oxidized glucose oxidase charged and that of SH-containing porous glass charged, according to the following equations:

Ratio of binding $(Y) = (A - B)/A$

Amount of bound glucose oxidase (mg per gram of porous glass) $= (Y \times D)/C$ where A = absorbance at 280 nm of the oxidized glucose oxidase solution before the reaction; B = absorbance at 280 nm of the supernatant after the reaction; C = amount of the SH-containing porous glass charged (g); D = amount of the oxidized glucose oxidase charged (mg).

EXAMPLE 3

Reaction of aldehyde group-containing glucose oxidase and cellulose

One gram of cellulose powder was thrown into the aldehyde group-containing glucose oxidase solution (50 ml) prepared by the method described in Reference Example 2 and containing about 100 mg of the aldehyde group-containing glucose oxidase. The reaction was allowed to proceed at room temperature with gentle stirring for 3 hours, and then the cellulose was filtered off and washed thoroughly with 1 M sodium chloride solution until no more enzyme activity could be detected in the washings. Finally the cellulose was washed with 0.01 M phosphate-buffered physiological saline (pH 7.3), immersed in the same saline and stored at 4° C. The amount of bound glucose oxidase was 68 mg per gram of cellulose (according to the calculation method described in Example 2).

COMPARATIVE EXAMPLE 1

Binding of glucose oxidase to amino-containing porous glass through glutaraldehyde Ten milliliters of aqueous 5% glutaraldehyde solution (pH 5) was added to 2 G of an NH$_2$-introduced porous glass (Pierce Chemical Co., USA; amino content: about 140 μM/g), and the mixture was maintained under a reduced pressure (50 or 100 mmHg) for 5 minutes to remove air bubbles in the porous glass. After the subsequent 30 minutes gentle stirring at room temperature, the supernatant was removed, and the glass was washed with deionized water until no more aldehyde odor could be smelled. Finally, it was washed once with 0.05 M phosphate buffer (pH 7.5). There was thus obtained an aldehyde group-containing porous glass.

A solution of 100 mg of glucose oxidase (Toyobo Co., LTd.) in 50 ml of 0.05 M phosphate buffer (pH 7.5) was added to the above aldehyde group containing porous glass, and the mixture was stirred gently for 3 hours while cooling the reaction vessel with ice water. After allowing the mixture to stand in a refrigerator overnight, the supernatant was removed; and the glass was washed well with aqueous 1 M soldium chloride solution. Finally it was washed with 0.01 M phosphate-buffered phsyiological sline (pH 7.3), immersed in the same saline and stored at 4° C.

The amount of the bound glucose oxidase was 23 mg per gram of the porous glass (according to the calculation method described in Example 2.

COMPARATIVE EXAMPLE 2

Reaction of aldehyde group-containing glucose oxidase and amino-containing porous glass Two grams of an NH$_2$-containing porous glass (Pierce Chemical Co.; amino content: about 140 μM/g) was thrown into the aldehyde group-containing glucose oxidase solution (50 ml) prepaed by oxidizing 100 mg of glucose oxidase (Toyobo Co., Ltd.) according to the method described in Reference Example 2 and containing about 100 mg of the aldehyde group-containing glucose oxidase. The mixture was kept under a reduced pressure (50 to 100 mmHg) at room temperature for 5 minutes so as to remove air bubbles in said porous glass. Then the reaction was allowed to proceed at room temperature with gentle stirring for 3 hours. After removal of the supernatant, the glass was washed well with 1 M sodium chloride solution, then washed with 0.01 M phosphate-buffered physiological saline (pH 7.3), immersed in the same saline and stored at 4° C.

The amount of the bound glucose oxidase was 35 mg per gram of the porous glass (according to the calculation method described in Example 2).

COMPARISON I

Comparative test for specific activity of the glucose oxidase derivatives

The glucose oxidase derivatives obtained in Example 2, and comparative Examples 1 and 2, were tested for specific enzyme activity, and the results were as shown in Table 1. The enzyme activity measurement was carried out according to the method described in Biochimica et Biophsica Acta 206, 54–60 (1970).

TABLE 1

| Glucose oxidase | Specific activity (units/mg of glycoprotein) |
| --- | --- |
| Untreated glucose oxidase | 43 |
| Derivative of Example 2 | 41 |
| Derivative of Comparative Example 1 | 28 |
| Derivative of Comparative Example 2 | 39 |

COMPARISON II

Storage stability test of the glucose oxidase derivatives

The glucose oxidase derivatives obtained in Example 2, and comparative Examples 1 and 2, respectively, were immersed in 0.01 M phosphate-buffered physiological saline (pH 7.3) and stored at 4° C., and were compared in respect of storage stability. The results are shown in Table 2. The activity measurement was made according to the method cited in Comparison I.

TABLE 2

| Glucose oxidase derivative of | Relative activity (%) | | | | | | |
|---|---|---|---|---|---|---|---|
| | Immediately after preparation | after | | | | | |
| | | one week | two weeks | one month | two months | six months | one year |
| Example 2 | 100 | 99.5 | 98.8 | 97.4 | 98.1 | 92.3 | 90.2 |
| Comparative Example 1 | 100 | 86.5 | 72.8 | 65.3 | 53.2 | 50.8 | 48.5 |
| Comparative Example 2 | 100 | 98.2 | 90.5 | 85.0 | 76.1 | 62.3 | 51.8 |

COMPARISON III

Thermal stability test of the glucose oxidase derivative

Untreated glucose oxidase (control) and the glucose oxidase derivative obtained in Example 2, respectively, were dissolved or immersed in 0.01 M phosphate-buffered physiological saline (pH 7.3), and stored at 60° C. The results of this thermal stability test are shown in Table 3.

TABLE 3

| Glucose oxidase | Relative activity (%) after hour(s) | | | | | | | | |
|---|---|---|---|---|---|---|---|---|---|
| | 0 | 0.5 | 1 | 2 | 3 | 4 | 5 | 10 | 20 | 48 |
| Untreated glucose oxidase | 100 | 48.2 | 26.5 | 10.5 | 5.6 | 2.8 | 1.6 | 0 | — | — |
| Derivative of Example 2 | 100 | 75.1 | 63.8 | 51.3 | 41.8 | 34.8 | 31.3 | 23.5 | 18.3 | 15.2 |

What is claimed as new and desired to be secured by Letters Patent is:

1. A process for producing a glyco-protein derivative composition, which comprises reacting an aldehyde group-containing glycoprotein (A) with at least one SH or OH group-containing material (B) forming hemithioacetal, hemiacetal, thioacetal, or acetal linkage when reacted under suitable conditions with said aldehyde group.

2. The process of claim 1, wherein (A) and (B) are reacted at a pH within the range of 3–10.

3. The process of claim 1, wherein (A) and (B) are reached at a temperature within the range of 0°–50° C.

4. The process of claim 1, wherein (B) is at least one material selected from the group consisting of thioalcohols, alcohols, peptides, natural or synthetic SH or OH group-containing polymers, and materials into which SH or OH groups have been introduced with a sulfhydrylating agent or a hydroxylating agent.

5. The process of claim 1, wherein (A) is reacted with (B) at one step.

6. The process of claim 1, wherein the reaction is carried out at two steps:
(1) reacting (A) with an SH or OH group-containing material ($B_1$), and
(2) thereafter reacting the reaction product with ($B_1$) or another SH or OH group-containing material ($B_2$).

7. The process of claim 1, wherein (B) is a water-insoluble SH or OH group-containing material.

8. The process of claim 1, wherein (B) is a water-soluble SH or OH group-containing material.

9. The process of claim 6, wherein ($B_1$) is a water-insoluble SH or OH group-containing material and ($B_2$) is a water-soluble SH or OH group-containing material.

10. The process of claim 1, wherein (B) is a water-insoluble SH or OH group-containing material obtained by reacting a sulfhydrylating agent or a hydroxylating agent with a solid material.

11. The process of claim 10, wherein the solid material is a material selected from the group consisting of glass, silica, metals, metal oxides and polymers.

12. The process of claim 11, wherein the polymer is an olefin polymer, a styrene polymer, an acrylic polymer, a polyurethane, a polyamide, a polyimide, a polyamino acid, a cellulose or a derivative thereof, or an agarose or a derivative thereof.

13. The process of claim 10, wherein the solid material is a porous material.

14. The process of claim 10, wherein the sulfhydrylating agent or hydroxylating agent is an SH group-containing silane coupling agent or an OH group-containing silane coupling agent.

15. The process of claim 1, wherein (B) is at least one water-soluble material selected from the group consisting of thioalcohols, alcohols, SH or OH group-containing peptides and SH or OH group-containing water soluble polymer.

16. The process of claim 15, wherein said peptides is an oligopeptide, an enzyme or an antibody.

17. The process of claim 15, wherein said peptide is an antibody.

18. The process of claim 15, wherein said peptide is a peptide having SH or OH groups, which have been introduced thereinto with a sulfhydrylating agent or hydroxylating agent.

19. The process of claim 15, wherein said peptide is an antibody having SH or OH groups, which are introduced with a sulfhydrylating agent or a hydroxylating agent.

20. The process of claim 18 or 19, wherein the sulfhydrylating agent or hydroxylating agent is an S-acylmercapto group-containing acid anhydride or an O-acylhydroxyl group-containing acid anhydride.

21. The process of claim 1, wherein (A) is a glycoprotein having at least one aldehyde group, which is formed by oxidizing a carbohydrate moiety of the glycoprotein with an oxidizing agent.

22. The process of claim 21, wherein the oxidizing agent is an oxygen acid or a salt thereof.

23. The process of claim 21, wherein the glycoprotein is an enzyme or an antibody.

24. The process of claim 23, wherein the enzyme is α-amylase, glucoamylase, β-galactosidase, glucose oxidase, peroxidase or invertase.

25. A glycoprotein derivative composition comprising an aldehyde group-containing glycoprotein (A) reacted with at least one SH or OH group-containing material (B) which forms hemithioacetal, hemiacetal, thioacetal or acetal linkage when contacted under suitable conditions with said aldehyde group.

26. A conjugate derived from an aldehyde group-containing glycoprotein (A), which comprises a glycoprotein covalently bound to at least one SH or OH group-containing material (B) which forms hemithioacetal, hemiacetal, thioacetal or acetal linkage when reacted under suitable conditions with said aldehyde group.

27. The process of claim 1, wherein (B) comprises a water-soluble SH or OH group-containing material or a combination thereof with a water-insoluble SH or OH group-containing material.

* * * * *